US011753622B2

(12) United States Patent
Yuan et al.

(10) Patent No.: US 11,753,622 B2
(45) Date of Patent: Sep. 12, 2023

(54) MEDIUM SUPPLEMENT TO INCREASE THE EFFICIENCY OF OOCYTE MATURATION AND EMBRYO CULTURE IN VITRO

(71) Applicants: Ye Yuan, Columbia, MO (US); Lee D. Spate, Columbia, MO (US); Randall S. Prather, Columbia, MO (US); R. Michael Roberts, Columbia, MO (US)

(72) Inventors: Ye Yuan, Columbia, MO (US); Lee D. Spate, Columbia, MO (US); Randall S. Prather, Columbia, MO (US); R. Michael Roberts, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 342 days.

(21) Appl. No.: 16/891,776

(22) Filed: Jun. 3, 2020

(65) Prior Publication Data

US 2021/0017490 A1     Jan. 21, 2021

Related U.S. Application Data

(63) Continuation of application No. 15/445,621, filed on Feb. 28, 2017, now abandoned.

(60) Provisional application No. 62/301,309, filed on Feb. 29, 2016.

(51) Int. Cl.
*C12N 5/075* (2010.01)

(52) U.S. Cl.
CPC ........ *C12N 5/0609* (2013.01); *C12N 2501/10* (2013.01); *C12N 2501/105* (2013.01); *C12N 2501/115* (2013.01)

(58) Field of Classification Search
CPC .......... C12N 2501/10; C12N 2501/105; C12N 2501/11; C12N 2501/115; C12N 2501/235; C12N 2501/31; C12N 2501/727; C12N 2517/04; C12N 2517/10; C12N 5/0604; C12N 5/0609
See application file for complete search history.

(56) References Cited

U.S. PATENT DOCUMENTS

| | | |
|---|---|---|
| 6,998,266 B2 | 2/2006 | Samarut et al. |
| 8,962,311 B2 | 2/2015 | Valarche et al. |
| 2005/0193435 A1 | 9/2005 | Robl et al. |
| 2011/0076253 A1 | 3/2011 | Snyder et al. |
| 2012/0127716 A1 | 5/2012 | Ono |
| 2013/0211186 A1 | 8/2013 | Oatley et al. |
| 2015/0064149 A1 | 3/2015 | West et al. |

OTHER PUBLICATIONS

Abeydeera et al., "Fertilization and subsequent development in vitro of pig oocytes inseminated in a modified tris-buffered medium with frozen-thawed ejaculated spermatozoa," *Biol Reprod*, 57(4):729-734, 1997.
Arici et al. "Leukaemia inhibitory factor expression in human follicular fluid and ovarian cells," *Hum Reprod*, 12(6):1233-1239, 1997.
Conti et al., "Novel signaling mechanisms in the ovary during oocyte maturation and ovulation," *Mol Cell Endocrinol*, 356(1-2):65-73, 2012.
Dalton, "Signaling networks in human pluripotent stem cells," *Curr Opin Cell Biol*, 25(2):241-246, 2013.
Dang-Nguyen et al., "Leukemia inhibitory factor promotes porcine oocyte maturation and is accompanied by activation of signal transducer and activator of transcription 3," *Mol Reprod Dev*, 81(3):230-239; 2014.
De Matos et al. "Leukemia inhibitory factor induces cumulus expansion in immature human and mouse oocytes and improves mouse two-cell rate and delivery rates when it is present during mouse in vitro oocyte maturation," *Fertil and Steril*, 90(6):2367-2375, 2008.
Evans et al., "Effects of fibroblast growth factor 9 on steroidogenesis and control of FGFR2IIIc mRNA in porcine granulosa cells," *J Anim Sci*, 92(2):511-519, 2014.
Fan et al. "MAPK3/1 (ERIK1/2) in ovarian granulosa cells are essential for female fertility," *Science*, 324(5929):938-941, 2009.
Feng et al., "Transforming growth factor-beta stimulates meiotic maturation of the rat oocyte," *Endocrinology*, 122(1):181-186, 1988.
Fukuda et al., "Insulin-like growth factor 1 induces hypoxia-inducible factor 1-mediated vascular endothelial growth factor expression, which is dependent on MAP kinase and phosphatidylinositol 3-kinase signaling in colon cancer cells," *J Biol Chem*, 277(41):38205-38211, 2002.
Gilchrist et al., "Oocyte-secreted factors: regulators of cumulus cell function and oocyte quality," *Hum Reprod Update*, 14(2):159-177, 2008.
Grupen et al. "Role of epidermal growth factor and insulin-like growth factor-I on porcine oocyte maturation and embryonic development in vitro," *Reprod Fertil Dev*, 9(6):571 575, 1997.
Grupen, "The evolution of porcine embryo in vitro production," *Theriogenology*, 81(1):24-37, 2014.
Hsieh et al., "Luteinizing hormone-dependent activation of the epidermal growth factor network is essential for ovulation," *Mol Cell Biol*, 27(5):1914-1924, 2007.
Hyttel et al., "Oocyte growth, capacitation and final maturation in cattle," *Theriogenology* 47(1):23-32, 1997.
Kiapekou et al,. "Effects of GH and IGF-I on the in vitro maturation of mouse oocytes," *Hormones*, 4(3):155-160, 2005.
Kooijman et al., "IGF-I stimulates IL-8 production in the promyelocytic cell line HL-60 through activation of extracellular signal-regulated protein kinase," *Cell Signal*, 15(12):1091-1098, 2003.

(Continued)

*Primary Examiner* — Blaine Lankford
(74) *Attorney, Agent, or Firm* — Dentons US LLP

(57) ABSTRACT

The present invention provides a novel oocyte maturation medium or/and embryo culture medium with a chemically defined supplement to produce matured oocytes at high efficiency. The inventive medium or supplement comprises three growth factors, namely, fibroblast growth factor 2 (FGF2), leukemia inhibitory factor (LIF), and insulin-like growth factor 1 (IGF-1) in a synergistic combination. Methods for oocyte and embryo culture are also provided.

22 Claims, 8 Drawing Sheets

(56) References Cited

OTHER PUBLICATIONS

Krisher et al., "Supplementation of growth factors during in vitro maturation improves oocyte developmental competence, although species differences exist," Presentation, Abstract 344, Society for the Study of Reproduction, 49th Annual Meeting, San Diego, CA, Jul. 16-20, 2016.
Kyriakis et al., "Mammalian mitogen-activated protein kinase signal transduction pathways activated by stress and inflammation," *Physiol Rev*, 81(2):807-869, 2001.
Kyriakis et al., "Mammalian MAPK signal transduction pathways activated by stress and inflammation: a 10-year update," *Physiol Rev*, 92(2):689-737, 2012.
LaRosa et al., "Stress stimulates AMP-activated protein kinase and meiotic resumption in mouse oocytes," *Biol Reprod*, 74(3):585-592, 2006.
LaRosa et al., "Meiotic induction by heat stress in mouse oocytes: involvement of AMP-activated protein kinase and MAPK family members," *Biol Reprod*, 76(3):476-486, 2007.
Le Naour et al., "Severely reduced female fertility in CD9-deficient mice," *Science*, 287(5451):319-321, 2000.
Lee et al,. "Piglets produced from cloned blastocysts cultured in vitro with GM-CSF," *Mol Reprod Dev*, 80(2):145-154, 2013.
Lonergan et al., "Maturation of oocytes in vitro," *Annu Rev Anim Biosci*, 4:255-268, 2016.
MacAulay et al,. "Cumulus Cell Transcripts Transit to the Bovine Oocyte in Preparation for Maturation," *Biol Reprod*, 94(1):16, 1-11 2016.
Malamitsi-Puchner et al,. "In vitro fertilization: angiogenic, proliferative, and apoptotic factors in the follicular fluid," *Ann N Y Acad Sci*, 997:124-128, 2003.
Mark et al., "Basic FGF attenuates amyloid beta-peptide-induced oxidative stress, mitochondrial dysfunction, and impairment of Na+/K+-ATPase activity in hippocampal neurons," *Brain Res*, 756(1-2):205-214, 1997.
Miyado et al., "Requirement of CD9 on the egg plasma membrane for fertilization," *Science*, 287(5451):321-324, 2000.
Mo et al., "Leukemia inhibitory factor enhances bovine oocyte maturation and early embryo development," *Mol Reprod Dev*, 81(7):608-618, 2014.
Mondal et al., "Effect of Fibroblast growth factor 2 (FGF2) and insulin transferrin selenium (ITS) on in vitro maturation, fertilization and embryo development in sheep," *Braz Arch Biol Techn*, 58(4):521-525, 2015.
Nicola et al., "Leukemia inhibitory factor (LIF)," *Cytokine Growth Factor Rev*, 26(5):533-544, 2015.
Nilsson et al., "Leukemia inhibitory factor (LIF) promotes the primordial to primary follicle transition in rat ovaries," *Mol Cell Endocrinol*, 188(1-2):65-73, 2002.
Nilsson et al., "Kit ligand and basic fibroblast growth factor interactions in the induction of ovarian primordial to primary follicle transition," *Mol Cell Endocrinol*, 214(1-2):19-25, 2004.
Norris et al,. "Cyclic GMP from the surrounding somatic cells regulates cyclic AMP and meiosis in the mouse oocyte," *Development*, 136(11):1869-1878, 2009.
Oka et al., "CD9 is associated with leukemia inhibitory factor-mediated maintenance of embryonic stem cells," *Mol Biol Cell*, 13(4):1274-1281, 2002.
Pandey et al., A moderate increase of hydrogen peroxide level is beneficial for spontaneous resumption of meiosis from diplotene arrest in rat oocytes cultured in vitro, *Biores Open Access*, 3(4):183-191, 2014.
Park et al., "EGF-like growth factors as mediators of LH action in the ovulatory follicle," *Science*, 303(5658):682-684, 2004.
Planavila et al., "Fibroblast growth factor 21 protects the heart from oxidative stress," *Cardiovasc Res*, 106(1):19-31, 2015.
Prochazka et al,. "Epidermal growth factor-receptor tyrosine kinase activity regulates expansion of porcine oocyte-cumulus cell complexes in vitro," *Biol Reprod*, 68(3):797-803, 2003.
Quetglas et al., "Effect of insulin-like growth factor-1 during in vitro oocyte maturation and in vitro culture of bovine embryos," *Arq Bras Med Vet Zoo*, 53(2):207-211, 2001.
Redel et al., "Arginine increases development of in vitro-produced porcine embryos and affects the protein arginine methyltransferase-dimethylarginine dimethylaminohydrolase-nitric oxide axis," *Reprod Fertil Dev*, 27(4):655-666, 2015.
Redel et al., "FGF2, Lif, and IGF-1 added together during maturation and culture improve somatic cell nuclear transfer embryo development and overall efficiency," Presentation, Abstract 345, Society for the Study of Reproduction, 49th Annual Meeting, San Diego, CA, Jul. 16-20, 2016.
Salhab et al. "In vitro maturation of oocytes alters gene expression and signaling pathways in bovine cumulus cells," *Mol Reprod Dev*, 80(2):166-182, 2013.
Sanchez et al., "Molecular control of oogenesis," *Biochim Biophys Acta*, 1822(12):1896-1912, 2012.
Sela-Abramovich et al., "Mitogen-activated protein kinase mediates luteinizing hormone-induced breakdown of communication and oocyte maturation in rat ovarian follicles," *Endocrinology*, 146(3):1236-1244, 2005.
Sela-Abramovich et al., "Disruption of gap junctional communication within the ovarian follicle induces oocyte maturation," *Endocrinology*, 147(5):2280-2286, 2006.
Shimada et al., "Luteinizing hormone receptor formation in cumulus cells surrounding porcine oocytes and its role during meiotic maturation of porcine oocytes," *Biol Reprod*, 68(4):1142-1149, 2003.
Shimada et al., "Paracrine and autocrine regulation of epidermal growth factor-like factors in cumulus oocyte complexes and granulosa cells: key roles for prostaglandin synthase 2 and progesterone receptor," *Mol Endocrinol*, 20(6):1352-1365, 2006.
Spate et al., "PS48 can replace bovine serum albumin in pig embryo culture medium, and improve in vitro embryo development by phosphorylating AKT," *Mol Reprod Dev*, 82(4):315-320, 2015.
Spate et al., "A combination of three growth factors can enhance porcine embryo development during in vitro culture," Presentation, Abstract 343, Society for the Study of Reproduction, 49th Annual Meeting, San Diego, CA, Jul. 16-20, 2016.
Spate et al., "In vitro-matured gilt oocytes can have equal or better developmental competence than sow oocytes with new maturation media," Presentation, Abstract 86, International Embryo Technology Society, 43rd Annual Meeting, Austin, TX, Jan. 14-17, 2017.
Su et al., "Mitogen-activated protein kinase activity in cumulus cells is essential for gonadotropin-induced oocyte meiotic resumption and cumulus expansion in the mouse," *Endocrinology*, 143(6):2221-2232, 2002.
Su et al., "Oocyte-dependent activation of mitogen-activated protein kinase (ERK1/2) in cumulus cells is required for the maturation of the mouse oocyte-cumulus cell complex," *Dev Biol*, 263(1):126-138, 2003.
Suzuki et al., "Dynamic changes of cumulus-oocyte cell communication during in vitro maturation of porcine oocytes," *Biol Reprod*, 63(3):723-729, 2000.
Tu et al., "IGF-I increases interferon-gamma and IL-6 mRNA expression and protein production in neonatal mononuclear cells," *Pediatr Res*, 46(6):748-754, 1999.
Upadhyay et al., "Fibroblast growth factor-10 attenuates H2O2-induced alveolar epithelial cell DNA damage: role of MAPK activation and DNA repair," *Am J Respir Cell Mol Biol*, 31(1):107-113, 2004.
Wrenzycki et al., "Maturation environment and impact on subsequent developmental competence of bovine oocytes," *Reprod Domest Anim*, 48 Suppl 1:38-43, 2013.
Yamashita et al. "Positive feedback loop between prostaglandin E2 and EGF-like factors is essential for sustainable activation of MAPK3/1 in cumulus cells during in vitro maturation of porcine cumulus oocyte complexes," *Biol Reprod*, 85(5):1073-1082, 2011.
Yoshioka et al., "Birth of piglets derived from porcine zygotes cultured in a chemically defined medium," *Biol Reprod*, 66(1):112-119, 2002.
Yuan et al., "In vitro maturation (IVM) of porcine oocytes," *Methods Mol Biol*, 825:183-198, 2012.

(56) References Cited

OTHER PUBLICATIONS

Yuan et al., "A combination of three cytokines enhances porcine oocyte in vitro maturation and development competence," Presentation, Abstract 531, Society for the Study of Reproduction, 49th Annual Meeting, San Diego, CA, Jul. 16-20, 2016.
Zhang et al., "Fibroblast growth factor 10 enhances bovine oocyte maturation and developmental competence in vitro," *Reproduction*, 140(6):815-826, 2010.
Zhang et al. "Porcine oocytes denuded before maturation can develop to the blastocyst stage if provided a cumulous cell-derived coculture system," *J Animal Sci*, 88(8):2604-2610, 2010.
Zhang et al., "Supplementing fibroblast growth factor 2 during bovine oocyte in vitro maturation promotes subsequent embryonic development," *Open J Anim Sci*, 02:119-126, 2012.

MEDIUM SUPPLEMENT TO INCREASE THE EFFICIENCY OF OOCYTE MATURATION AND EMBRYO CULTURE IN VITRO

CROSS-REFERENCE TO RELATED APPLICATIONS

This application is a continuation of U.S. patent application Ser. No. 15/445,621, filed on Feb. 28, 2017 (pending) which claims the benefit of priority of U.S. Provisional Application No. 62/301,309, filed on Feb. 29, 2016, the disclosure each of which is hereby incorporated by reference in its entirety.

STATEMENT REGARDING FEDERALLY SPONSORED RESEARCH

This invention was made with Government support under Grant No. RO1 HD069979 awarded by the National Institutes of Health. The Government has certain rights in the invention.

FIELD OF THE INVENTION

The present invention relates to methods and compositions for reproductive technology, more particularly to media and methods for oocyte maturation or embryo culture.

BACKGROUND OF THE INVENTION

The statements in this section merely provide background information related to the present disclosure and may not constitute prior art.

Cloning pigs by somatic cell nuclear transfer (SCNT) or in vitro fertilization (IVF) has wide applications in basic research, human medicine and agricultural production. However, the rate of in vitro development of porcine oocytes and embryos to blastocysts is very low (10-15%) when compared to oocytes that are matured and fertilized in vivo. Further, when such blastocysts are transferred to surrogates, only a low fraction (~10%) give rise to piglets. Overall success of producing offspring, therefore is in the order of 1%. This low efficiency can, therefore, be attributed to the poor quality of the initiating oocytes as a result of inadequate in vitro maturation. Some studies indicate that the mRNA profile (transcriptome), cellular protein composition (proteome), and other features of the oocyte and its surrounding somatic cells (cumulus cells) can be influenced by the composition of maturation media and contribute to oocyte maturation and subsequent in vitro embryonic development.

Therefore, there is a need to provide a new and improved oocyte maturation medium or/and embryo culture medium to increase significantly the efficiency of producing matured oocytes and viable blastocysts in vitro.

SUMMARY OF THE INVENTION

In one aspect the present invention provides a medium for culturing an oocyte comprising fibroblast growth factor 2 (FGF2), leukemia inhibitory factor (LIF), and insulin-like growth factor 1 (IGF-1) in an amount effective to support culture of an oocyte therein. In one embodiment, the medium does not comprise follicular fluid or serum. In another embodiment, the medium is an oocyte maturation medium and supports maturation of an oocyte cultured therein. In a further embodiment, the medium is an in vitro fertilization medium and supports in vitro fertilization of an oocyte performed therein. In yet another embodiment, the medium is a cumulus oocyte complex culture medium and supports culture of a cumulus oocyte complex cultured therein.

In still a further embodiment, the medium is a liquid medium, a solid medium, or a medium comprising a solid support. In another embodiment, the medium comprises an oocyte or a plurality of oocytes.

In another aspect, the present invention provides a method of oocyte maturation, said method comprising contacting an immature oocyte with a medium of the invention comprising fibroblast growth factor 2 (FGF2), leukemia inhibitory factor (LIF), and insulin-like growth factor 1 (IGF-1).

In yet another aspect, the present invention provides a method of improving the developmental competence of an oocyte or an embryo produced from an oocyte, said method comprising contacting the oocyte with a medium of the invention comprising fibroblast growth factor 2 (FGF2), leukemia inhibitory factor (LIF), and insulin-like growth factor 1 (IGF-1).

In a further aspect, the present invention provides a method of embryo transfer, said method comprising a) contacting an oocyte with a medium of the invention comprising fibroblast growth factor 2 (FGF2), leukemia inhibitory factor (LIF), and insulin-like growth factor 1 (IGF-1); b) producing an embryo from said oocyte; and c) transferring said embryo to the uterus of a recipient female.

In yet a further aspect, the present invention provides a method of assisted reproduction, said method comprising contacting an oocyte with a medium of the invention comprising fibroblast growth factor 2 (FGF2), leukemia inhibitory factor (LIF), and insulin-like growth factor 1 (IGF-1). In one embodiment, the assisted reproduction comprises in vitro fertilization or somatic cell nuclear transfer (SCNT).

In another aspect, the present invention provides a medium for culturing an embryo comprising fibroblast growth factor 2 (FGF2), leukemia inhibitory factor (LIF), and insulin-like growth factor 1 (IGF-1), in an amount effective to support zygote development to a blastocyst. In one embodiment, the medium is a liquid medium, a solid medium or comprises a solid support. In another embodiment, the medium comprises a zygote, an embryo, a plurality of zygotes, or a plurality of embryos.

In another aspect, the present invention provides a method of improving developmental competence of an embryo, said method comprising contacting a zygote or an embryo with a medium of the invention comprising fibroblast growth factor 2 (FGF2), leukemia inhibitory factor (LIF), and insulin-like growth factor 1 (IGF-1).

In yet a further aspect, the present invention provides a method of embryo transfer, said method comprising contacting an embryo with a medium of the invention comprising fibroblast growth factor 2 (FGF2), leukemia inhibitory factor (LIF), and insulin-like growth factor 1 (IGF-1) prior to transfer of said embryo to the uterus of a recipient female.

BRIEF DESCRIPTION OF THE DRAWINGS

The drawings described herein are for illustration purposes only and are not intended to limit the scope of the present teachings in any way.

DETAILED DESCRIPTION OF THE INVENTION

Figure 1:
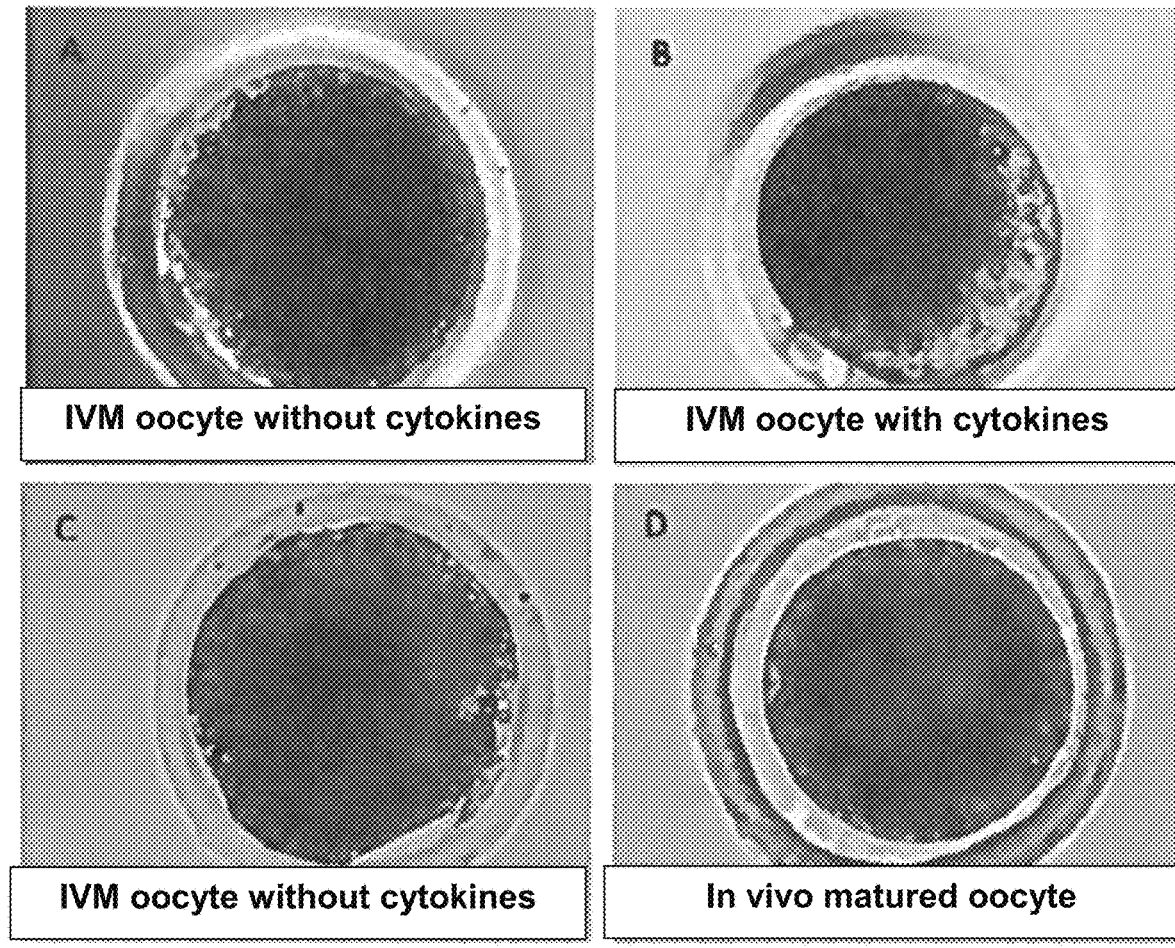
FIG. 1. Representative images of porcine oocytes matured in vitro with (panel B) or without (panels A, and C) the supplementation of cytokines (fibroblast growth factor 2 (FGF2), leukemia inhibitory factor (LIF), and insulin-like growth factor 1 (IGF-1)), in comparison with in vivo matured oocyte (panel D).

The following description is merely exemplary in nature and is in no way intended to limit the present teachings, application, or uses.

The present invention provides novel media and methods for oocyte maturation and embryo culture. In particular, the present invention provides a medium with an added supplement of fibroblast growth factor 2 (FGF2), leukemia inhibitory factor (LIF), and insulin-like growth factor 1 (IGF-1) in amounts effective to support culture of an immature oocyte and its surrounding cumulus cells such that the oocyte is competent to be fertilized, develop to the blastocyst stage, and give rise to live animals. In one embodiment, the media of the present invention comprise FGF2, LIF, and IGF-1 in a synergistic combination.

Oocyte in vitro maturation (IVM) is a critical step in assisted reproductive technologies (ART) in producing developmentally competent oocytes for agricultural purposes. It is also important for human in vitro fertilization (IVF) under conditions where high level exposure of the patient to superovulating regimens of hormones is counter-indicated. However, the attainment of development competency in such IVM oocytes as compared to their in vivo counterparts continues to be a challenge in the art, particularly if the oocytes are derived from immature animals. The present invention overcomes this problem the art. In one embodiment, the present invention provides an oocyte culture medium comprising three cytokines (FGF2, LIF, and IGF-1) that improves in vitro oocyte maturation, subsequent embryo or blastocyst developmental competence, and viability of oocytes for agricultural and human biomedical purposes.

In certain embodiments, the present invention provides media and methods for producing matured oocytes for subsequent use in somatic cell nuclear transfer (SCNT) to efficiently produce blastocysts from zygotes generated via SCNT following oocyte maturation in a medium of the present invention. SCNT is a technique often used to produce genetically engineered animals that relies upon appropriately matured oocytes.

In still further embodiments, the media comprising the FGF2, LIF, and IGF-1 cytokines may also be used for embryo culture. In other embodiments, the oocyte maturation and/or the embryo culture media and methods of the present invention may improve embryo transfer, implantation, and fetal development after embryo transfer. For instance, as described in the Examples below, the media and methods of the present invention doubled the success in generating quality blastocysts for embryo transfer.

The FGF2, LIF, and IGF-1 cytokines may be supplemented or added to any standard or suitable oocyte culture media, such as oocyte maturation media or IVF media, or any standard or suitable embryo culture media. Standard media, conditions, and methods for oocyte culture, oocyte IVM, IVF, embryo culture, and SCNT are well known in the art and would be known by those of skill in the art. In certain embodiments, standard media for oocyte and embryo culture may comprise, but are not limited to Tissue Culture Media (TCM) 199, NCSU23 media, porcine zygote medium-3 (PZM-3), and MU1-PZM.

In certain embodiments, the FGF2, LIF, and IGF-1 cytokines may be formulated, prepared, or packaged in a manner suitable for supplementation to a standard culture medium. Media comprising FGF2, LIF, and IGF-1, or media supplementation comprising FGF2, LIF, and IGF-1, and the other various components or products of the present invention may be packaged separately in suitable containers (preferably sterilized) such as ampoules, bottles, or vials, either in multi-use or in unit forms. The containers may be hermetically sealed after being filled. Methods for packaging the various components are known in the art.

The media and methods described herein are generally applicable to oocytes and embryos, as well as donor cells for SCNT and recipient females for embryo transfer, from a wide array of mammalian animals, including, but not limited to, a primate or human, a livestock animal (such as, but not limited to, a pig, cow, horse, sheep, or goat), a companion animal (such as, but not limited to, a dog or cat), a laboratory test animals (such as, but not limited to, a mouse, rat, or guinea pig).

Although not intending bound by any theory, it is believed that the FGF2, LIF, and IGF-1 cytokines work synergistically in promoting oocyte competence by a mechanism that involves temporal fluctuations of activated MAPK. These events in turn control metabolic activity in CCs, resulting in the preservation of TZPs during early phase maturation and timely breakdown of TZPs at a later phase. Such features of IVM are likely conserved across species, such that the benefits in porcine and mouse oocyte IVM, described in the below Examples, can be translated to other species, such as cattle and human.

Media of the present invention may therefore comprise FGF2, LIF, and IGF-1 cytokines, the concentration of which may vary depending on the animal species. In certain embodiments, media of the present invention may comprise about 0.5 to 200 ng/ml of each of FGF2, LIF, or IGF-1, in combination. For instance, media of the present invention may comprise from about 0.5 to about 200 ng/ml, about 1 to about 200 ng/ml, about 2.5 to about 200 ng/ml, about 5 to about 200 ng/ml, about 10 to about 200 ng/ml, about 15 to about 200 ng/ml, about 20 to about 200 ng/ml, about 25 to about 200 ng/ml, about 30 to about 200 ng/ml, about 35 to about 200 ng/ml, about 40 to about 200 ng/ml, about 45 to about 200 ng/ml, about 50 to about 200 ng/ml, about 55 to about 200 ng/ml, about 60 to about 200 ng/ml, about 65 to about 200 ng/ml, about 70 to about 200 ng/ml, about 75 to about 200 ng/ml, about 80 to about 200 ng/ml, about 85 to about 200 ng/ml, about 90 to about 200 ng/ml, about 95 to about 200 ng/ml, about 100 to about 200 ng/ml, 105 to about 200 ng/ml, about 110 to about 200 ng/ml, about 115 to about 200 ng/ml, about 120 to about 200 ng/ml, about 125 to about 200 ng/ml, about 130 to about 200 ng/ml, about 135 to about 200 ng/ml, about 140 to about 200 ng/ml, about 145 to about 200 ng/ml, about 150 to about 200 ng/ml, about 155 to about 200 ng/ml, about 160 to about 200 ng/ml, about 165 to about 200 ng/ml, about 170 to about 200 ng/ml, about 175 to about 200 ng/ml, about 180 to about 200 ng/ml, about 185 to about 200 ng/ml, about 190 to about 200 ng/ml, about 195 to about 200 ng/ml, about 0.5 to about 195 ng/ml, about 0.5 to about 190 ng/ml, about 0.5 to about 185 ng/ml, about 0.5 to about 180 ng/ml, about 0.5 to about 175 ng/ml, about 0.5 to about 170 ng/ml, about 0.5 to about 165 ng/ml, about 0.5 to about 160 ng/ml, about 0.5 to about 155 ng/ml, about 0.5 to about 150 ng/ml, about 0.5 to about 145 ng/ml, about 0.5 to about 140 ng/ml, about 0.5 to about 135 ng/ml, about 0.5 to about 130 ng/ml, about 0.5 to about 125 ng/ml, about 0.5 to about 120 ng/ml, about 0.5 to about 115 ng/ml, about 0.5 to about 110 ng/ml, about 0.5 to about 105 ng/ml, about 0.5 to about 100 ng/ml, about 0.5 to about 95 ng/ml, about 0.5 to about 90 ng/ml, about 0.5 to about 85 ng/ml, about 0.5 to about 80 ng/ml, about 0.5 to about 75 ng/ml, about 0.5 to about 70 ng/ml, about 0.5 to about 65 ng/ml, about 0.5 to about 60 ng/ml, about 0.5 to about 55 ng/ml, about 0.5 to about 50 ng/ml, about 0.5 to about 45 ng/ml, about 0.5 to about 40 ng/ml, about 0.5 to about 35 ng/ml, about 0.5 to about 30 ng/ml, about 0.5 to about 25 ng/ml, about 0.5 to about 20 ng/ml, about 0.5 to about 15 ng/ml, about 0.5 to about 10 ng/ml, about 0.5 to about 5 ng/ml, about 0.5 to about 2.5 ng/ml, about 0.5 to about 1 ng/ml, about 0.5 to about 200 ng/ml, about 1 to about 195 ng/ml, about 2.5 to about 190 ng/ml, about 5 to about 185 ng/ml, about 10 to about 180 ng/ml, about 15 to about 175 ng/ml, about 20 to about 170 ng/ml, about 25 to about 165 ng/ml, about 30 to about 160 ng/ml, about 35 to about 155 ng/ml, about 40 to about 150 ng/ml, about 45 to about 145 ng/ml, about 50 to about 140 ng/ml, about 55 to about 135 ng/ml, about 60 to about 130 ng/ml, about 65 to about 125 ng/ml, about 70 to about 120 ng/ml, about 75 to about 115 ng/ml, about 80 to about 110 ng/ml, about 85 to about 105 ng/ml, about 90 to about 100 ng/ml, about 95 to about 100 ng/ml, or about 90 to about 95 ng/ml of FGF2; about 1 to about 100 ng/ml, about 5 to about 100 ng/ml, about 10 to about 100 ng/ml, about 15 to about 100 ng/ml, about 20 to about 100 ng/ml, about 25 to about 100 ng/ml, about 30 to about 100 ng/ml, about 35 to about 100 ng/ml, about 40 to about 100 ng/ml, about 45 to about 100 ng/ml, about 50 to about 100 ng/ml, about 55 to about 100 ng/ml, about 60 to about 100 ng/ml, about 65 to about 100 ng/ml, about 70 to about 100 ng/ml, about 75 to about 100 ng/ml, about 80 to about 100 ng/ml, about 85 to about 100 ng/ml, about 90 to about 100 ng/ml, about 95 to about 100 ng/ml, about 1 to about 95 ng/ml, about 1 to about 90 ng/ml, about 1 to about 85 ng/ml, about 1 to about 80 ng/ml, about 1 to about 75 ng/ml, about 1 to about 70 ng/ml, about 1 to about 65 ng/ml, about 1 to about 60 ng/ml, about 1 to about 55 ng/ml, about 1 to about 50 ng/ml, about 1 to about 45 ng/ml, about 1 to about 40 ng/ml, about 1 to about 35 ng/ml, about 1 to about 30 ng/ml, about 1 to about 25 ng/ml, about 1 to about 20 ng/ml, about 1 to about 15 ng/ml, about 1 to about 10 ng/ml, about 1 to about 5 ng/ml, about 5 to about 95 ng/ml, about 10 to about 90 ng/ml, about 15 to about 85 ng/ml, about 20 to about 80 ng/ml, about 25 to about 85 ng/ml, about 30 to about 80 ng/ml, about 35 to about 75 ng/ml, about 40 to about 70 ng/ml, about 45 to about 65 ng/ml, about 50 to about 60 ng/ml, or about 50 to about 55 ng/ml of LIF; and 1 to about 100 ng/ml, about 5 to about 100 ng/ml, about 10 to about 100 ng/ml, about 15 to about 100 ng/ml, about 20 to about 100 ng/ml, about 25 to about 100 ng/ml, about 30 to about 100 ng/ml, about 35 to about 100 ng/ml, about 40 to about 100 ng/ml, about 45 to about 100 ng/ml, about 50 to about 100 ng/ml, about 55 to about 100 ng/ml, about 60 to about 100 ng/ml, about 65 to about 100 ng/ml, about 70 to about 100 ng/ml, about 75 to about 100 ng/ml, about 80 to about 100 ng/ml, about 85 to about 100 ng/ml, about 90 to about 100 ng/ml, about 95 to about 100 ng/ml, about 1 to about 95 ng/ml, about 1 to about 90 ng/ml, about 1 to about 85 ng/ml, about 1 to about 80 ng/ml, about 1 to about 75 ng/ml, about 1 to about 70 ng/ml, about 1 to about 65 ng/ml, about 1 to about 60 ng/ml, about 1 to about 55 ng/ml, about 1 to about 50 ng/ml, about 1 to about 45 ng/ml, about 1 to about 40 ng/ml, about 1 to about 35 ng/ml, about 1 to about 30 ng/ml, about 1 to about 25 ng/ml, about 1 to about 20 ng/ml, about 1 to about 15 ng/ml, about 1 to about 10 ng/ml, about 1 to about 5 ng/ml, about 5 to about 95 ng/ml, about 10 to about 90 ng/ml, about 15 to about 85 ng/ml, about 20 to about 80 ng/ml, about 25 to about 85 ng/ml, about 30 to about 80 ng/ml, about 35 to about 75 ng/ml, about 40 to about 70 ng/ml, about 45 to about 65 ng/ml, about 50 to about 60 ng/ml, or about 50 to about 55 ng/ml of IGF-1 in combination.

In further embodiments, media of the present invention may comprise about 0.5 ng/ml, about 1 ng/ml, about 5 ng/ml, about 10 ng/ml, about 15 ng/ml, about 20 ng/ml, about 25 ng/ml, about 30 ng/ml, about 35 ng/ml, about 40 ng/ml, about 45 ng/ml, about 50 ng/ml, about 55 ng/ml, about 60 ng/ml, about 65 ng/ml, about 70 ng/ml, about 75 ng/ml, about 80 ng/ml, about 85 ng/ml, about 90 ng/ml, about 95 ng/ml, about 100 ng/ml, about 105 ng/ml, about 110 ng/ml, about 115 ng/ml, about 120 ng/ml, about 125 ng/ml, about 130 ng/ml, about 135 ng/ml, about 140 ng/ml, about 145 ng/ml, about 150 ng/ml, about 155 ng/ml, about 160 ng/ml, about 165 ng/ml, about 170 ng/ml, about 175 ng/ml, about 180 ng/ml, about 185 ng/ml, about 190 ng/ml, about 195 ng/ml, or about 200 ng/ml, of each of FGF2, LIF, or IGF-1, in combination. In still another embodiment, media of the present invention may comprise at least two of FGF2, LIF, or IGF-1 at any of the above concentrations.

In one embodiment, the present invention teaches that the addition of a supplement of three cytokines (FGF2, LIF, and IGF-1) to a chemically defined, but standard, medium for maturing oocytes can more than double the number of blastocysts generated by IVM/IVF procedures. In another embodiment, the invention also demonstrates that the matured oocytes generated in the initial maturation step better resemble in vivo matured oocytes in morphology than those generated without addition of the cytokines. In further embodiments, the blastocysts produced with the protocols of the invention, with the three cytokines present in the maturation medium, have a significantly higher number of cells than the controls, indicating that they, like the oocytes from which they are derived, might also have increased developmental potential.

Definitions

The term "oocyte maturation" as used herein refers the process whereby an oocyte progresses from a meiotically immature state, incapable of being fertilized, to an oocyte that is meiotically mature, capable of being fertilized, and of producing a viable embryo. The term may also refer to maturation of oocyte cytoplasm, such that the oocyte is able to support embryo development post-fertilization. In this regard, in certain embodiments of the invention, the oocyte may be present in vitro, such as an oocyte isolated from a female subject. A variety of oocytes may be selected for maturation. For example, in certain embodiments, oocytes may be isolated from a pre- or peri-pubertal animal, such as a gilt, heifer, or other livestock animal. In another embodiment, oocytes may be isolated from a human female subject.

The term "isolated" as used herein in reference to an oocyte, embryo, or cell refers to an oocyte, embryo or cell that has been separated or recovered from one or more components of its natural environment. An example of an isolated oocyte may be an oocyte isolated from a female subject. Such an isolated oocyte may be associated with a follicle, a cumulus oocyte complex, one or more cumulus cells (CCs), or may be denuded oocyte. An example of an isolated embryo may be an embryo produced in vitro using an assisted reproduction technology or an embryo isolated from a subject.

The term "female subject" as used herein refers to a female mammal including a primate or human, a livestock animal (such as, but not limited to, a pig, cow, horse, sheep, or goat), a companion animal (such as, but not limited to, a dog or cat), a laboratory test animals (such as, but not limited to, a mouse, rat, or guinea pig), or any other female mammal in which oocytes may be isolated and cultured.

The term "assisted reproduction" as used herein refers to any in vitro technique for maturing oocytes, fertilizing oocytes, producing zygotes, or producing embryos in animals and/or humans, including, but not limited to techniques using an oocyte or embryo cultured in vitro (such as in vitro maturation of an oocyte), in vitro fertilization (IVF), somatic cell nuclear transfer (SCNT); gamete intrafallopian transfer (GIFT), zygote intrafallopian transfer (ZIFT), tubal embryo transfer (TET), peritoineal oocyte and sperm transfer (POST), intracytoplasmic sperm injection (ICSI).

The term "developmental competence" as used herein in one embodiment refers to the capacity of an oocyte to develop into a blastocyst or embryo. In another embodiment, the term refers to the capacity of a blastocyst or embryo to develop into a viable animal. In certain embodiments, an oocyte or embryo with improved developmental competence will have an increased probability of developing into a live animal or human after successful implantation.

The term "cumulus cell" or "CC" as used herein refers to any cultured or non-cultured cell that is isolated from cells and/or tissue surrounding an oocyte. Those skilled in the art can readily identify a cumulus cell. Methods of isolating and culturing cumulus cells are known in the art.

The terms "culture" or "culturing" as used herein with respect to oocytes, zygotes, or embryos refer to laboratory procedures that involve placing an oocyte, zygote, or embryo in a culture medium. Methods and culture media suitable for culturing oocytes, zygotes, or embryos are well known to those skilled in the art.

The terms "suitable medium" or "standard medium" as used herein refer to any oocyte, zygote, or embryo culture medium. For instance, in one embodiment, a "suitable medium" or "standard medium" for oocyte maturation is that known in the art that allows for maturation of an immature oocyte to a mature oocyte capable of fertilization under suitable oocyte maturation conditions. In another embodiment, a "suitable medium" or "standard medium" for embryo culture is that known in the art that allows for the desired cell proliferation or stasis of an embryo under suitable embryo culture conditions.

The term "nucleic acid" as used throughout the specification is to be understood to mean to any oligonucleotide or polynucleotide. The nucleic acid may be DNA or RNA and may be single stranded or double stranded. The nucleic acid may be any type of nucleic acid, including a nucleic acid of genomic origin, cDNA origin (i.e. derived from a mRNA), derived from a virus, or of synthetic origin.

EXAMPLES

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the invention.

Example 1

Evaluation of Cytokines Individually in IVM Medium

Figure 2:
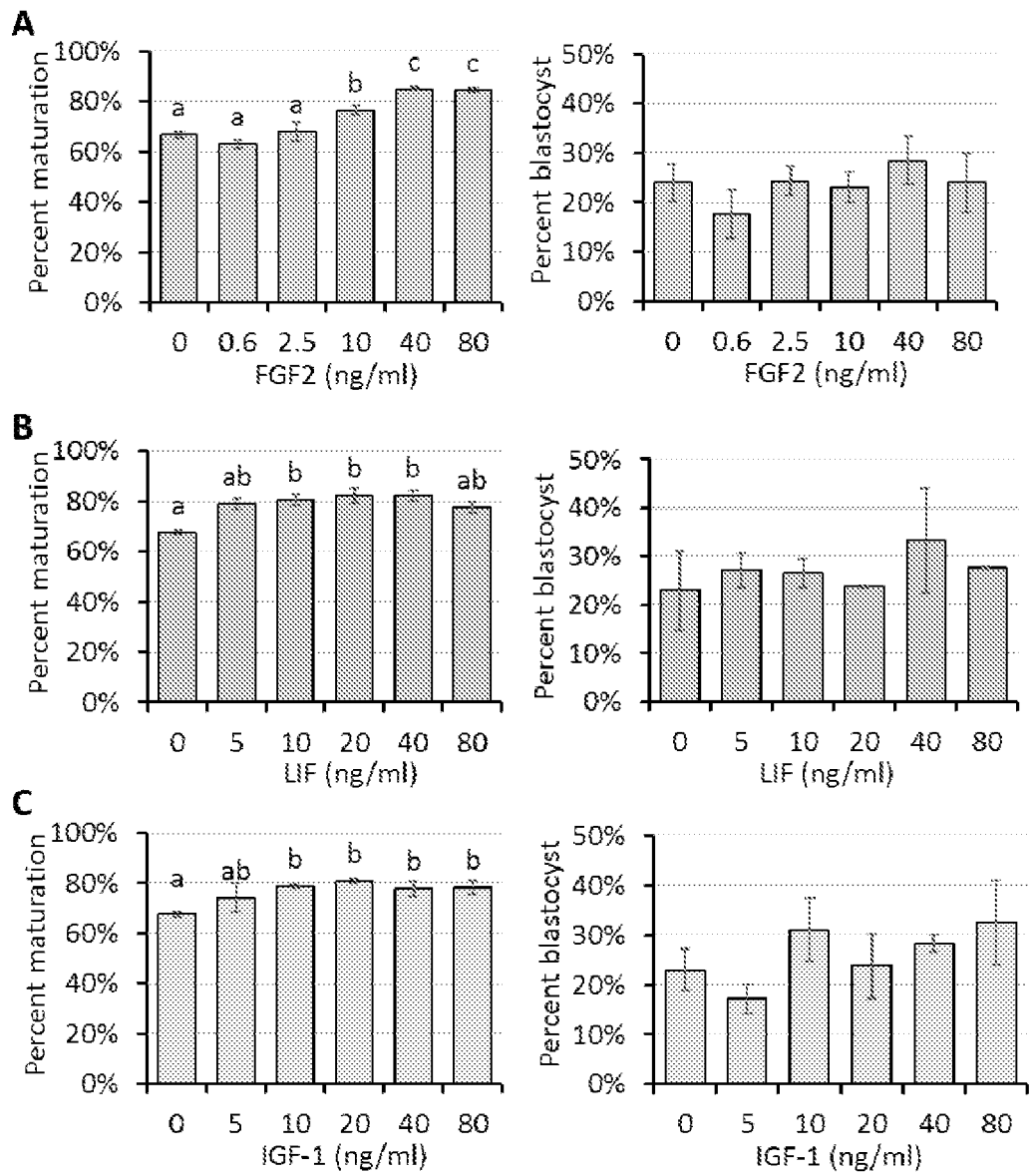
FIG. 2. Effects of various concentrations of FGF2 (panel A), LIF (panel B), and IGF-1 (panel C) in porcine oocyte maturation medium on nuclear maturation and subsequent developmental competence. Data are reported as means±SEM$^{ab}$. Different superscripts denote a significant difference from the control, P<0.05. The experiments were replicated four times with a total of 3558 oocytes.

The individual effects of FGF2, LIF, and IGF-1 on maturation of oocytes derived from pre-pubertal pre-pubertal gilts after commercial slaughter were examined after each had been added to an otherwise standard, chemically-defined medium comprised of TCM 199 supplemented with 10 ng/ml EGF, 0.5 μg/ml LH, 0.5 μg/ml FSH, 3.05 mM glucose, 0.91 mM sodium pyruvate, 0.57 mM cysteine, 10 ng/mL gentamicin, and 0.1% polyvinyl alcohol (PVA). After 42 hr in the oocyte maturation medium with the single cytokine addition, oocytes were in vitro fertilized and the resulting zygotes were cultured under standard in vitro culture conditions for 6 days. While each of FGF2, LIF, and IGF-1, individually improved the efficiency of producing nuclear matured, i.e. metaphase II (MII), oocytes, none of the cytokines improved oocyte developmental competence, as determined by the ability of the fertilized oocytes (zygotes) to form blastocysts after IVF. (FIG. 2).

Example 2

Evaluation of Cytokines in Combination in IVM Medium

Optimal concentrations of FGF2 (40 ng/ml) and LIF (20 ng/ml) were added in combination to the standard IVM medium. The combination of FGF2 and LIF improved nuclear maturation beyond that achieved with the single factors in Example 1 (Table 1). In addition, these matured oocytes had improved developmental competence to form blastocysts, as demonstrated by the increased number of blastocyst-stage embryos (Table 1, column 5, 6).

Figure 5:
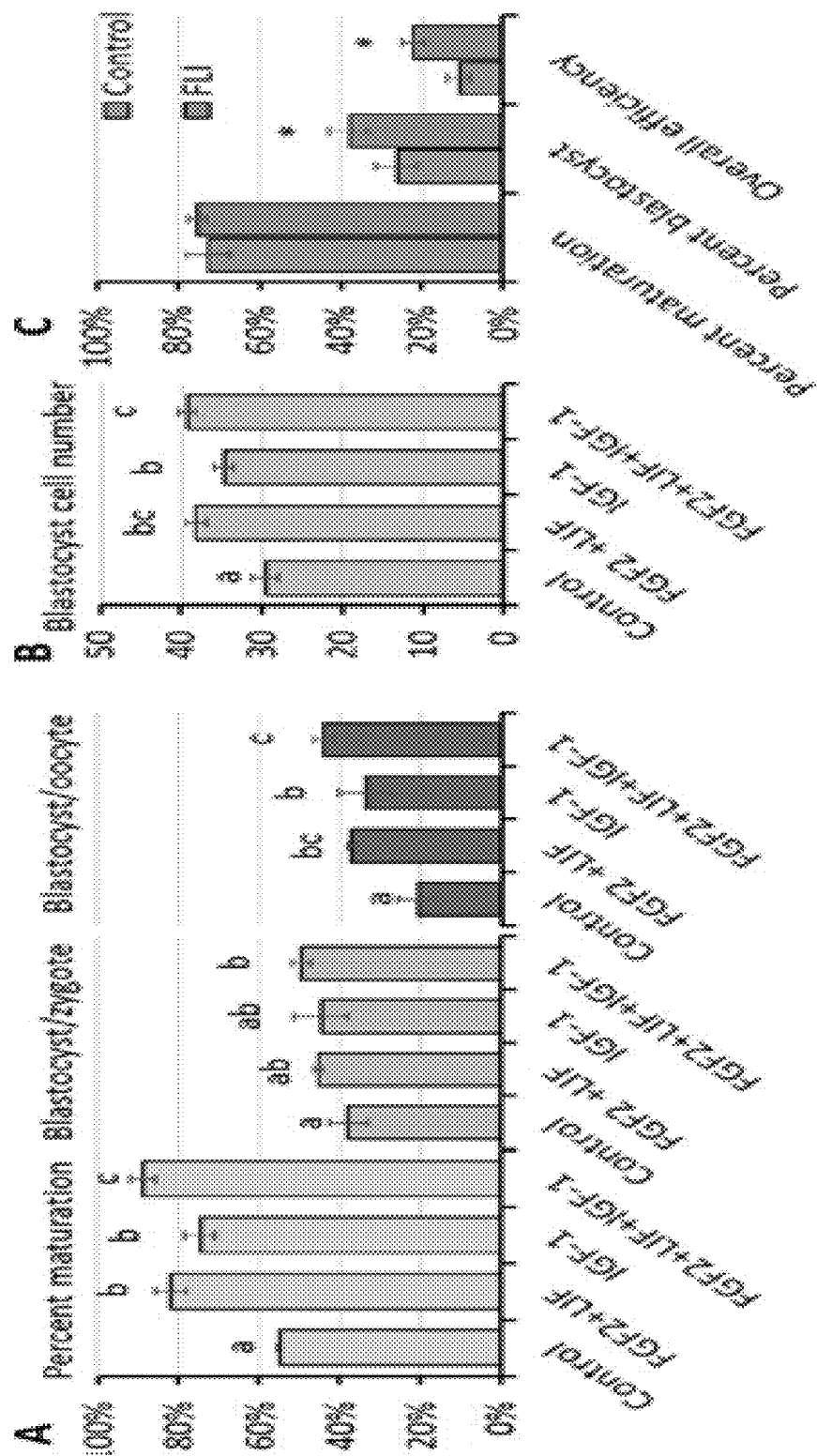
FIG. 5. Supplementation of FGF2, LIF and IGF-1 (FLI) in IVM medium improves porcine oocyte meiotic maturation and developmental competence. Panels A and B show the effects of FLI in porcine IVM medium on nuclear maturation and subsequent blastocyst development following IVF. The experiments were replicated four times with total of 796 oocytes. Different letters denote significant differences, P<0.05. Panel C shows supplementation of FLI in IVM medium improved blastocyst development following somatic cell nuclear transfer (SCNT). The experiments were replicated five times with a total of 488 oocytes. The left hand bar for each set represents controls; the right hand bar for each set represents treatment with cytokines Asterisk denotes a significant difference between control and treatment, P<0.05.

The effects of adding the IGF-1 at the optimal concentration of 20 ng/ml in combination with the other two cytokines to the IVM medium was then examined. The combination of all three cytokines (FGF2, LIF, and IGF-1) increased oocyte nuclear maturation to 89%, as compared to 55% in controls (FIG. 5 and Table 2, column 4). After IVF, zygotes from oocytes cultured in medium comprising FGF2, LIF, and IGF-1 advanced to the blastocyst stage more efficiently than controls (49.7% versus 38%). This protocol, requiring all three cytokines during the maturation phase, led to over a two-fold increase in the number of blastocysts produced per 100 oocytes retrieved from the ovaries (Table 2, column 6). Blastocyst cell number also increased, suggesting that embryo quality likely improved, as well (FIG. 5, and Table 2, column 7). Overall, the use of medium comprising FGF2, LIF, and IGF-1 during oocyte maturation, led to over a two-fold increase in the number of blastocyst stage. Oocytes derived from medium comprising FGF2, LIF, and IGF-1 also provided improved production of blastocysts following somatic cell nuclear transfer (SCNT), which requires removal of nuclear material from the egg followed by fusion of the enucleated oocyte with a somatic donor cell (FIG. 5).

Furthermore, when the same number of embryos produced from the same number of retrieved oocytes of IVF and cloned blastocysts were transferred to surrogate gilts, the blastocysts from the oocytes that had been treated by the combination of FGF2, LIF, and IGF-1, appeared to be more competent to develop in vivo and yield healthy piglets with larger litter size than those from non-treated oocytes and none of the resulting piglets showed obvious developmental abnormalities (Table 3, column 4).

TABLE 1

Effects of FGF2 and LIF in porcine oocyte maturation medium on nuclear maturation and subsequent developmental competence*.

| Treatment | Replicates (n) | Oocytes (n) | Nuclear Maturation (%) | Blastocysts/ Zygote (%) | Blastocysts/ Oocyte (%) |
|---|---|---|---|---|---|
| Control | 5 | 350 | $61.8 \pm 6.0^b$ | $30.2 \pm 1.8^{ab}$ | $18.6 \pm 2.1^b$ |
| FGF2 | 5 | 350 | $73.2 \pm 3.4^a$ | $35.1 \pm 4.9^a$ | $25.6 \pm 3.6^{ab}$ |
| LIF | 5 | 354 | $75.7 \pm 3.1^a$ | $25.4 \pm 4.0^b$ | $19.6 \pm 3.6^{ab}$ |
| FGF2 + LIF | 5 | 401 | $77.9 \pm 3.6^a$ | $36.9 \pm 4.4^a$ | $28.9 \pm 3.8^a$ |

*Data are reported as means ± SEM
$^{ab}$Different superscripts within a column denote a significant difference, P < 0.05.

TABLE 2

Effects of FGF2, LIF, and IGF-1, together and in combination, in porcine oocyte maturation medium on nuclear maturation and subsequent developmental competence.*

| Treatment | Replicates (n) | Oocytes (n) | Nuclear Maturation (%) | Blastocysts/ Zygote (%) | Blastocysts/ Oocyte (%) | Total blastocyst cell number |
|---|---|---|---|---|---|---|
| Control | 4 | 196 | $55.1 \pm 0.5^c$ | $38.0 \pm 8.9^b$ | $20.9 \pm 4.4^c$ | $29.6 \pm 1.1^c$ |
| FGF2 + LIF | 4 | 199 | $81.9 \pm 3.9^b$ | $45.3 \pm 1.1^{ab}$ | $37.2 \pm 2.5^{ab}$ | $38.1 \pm 1.3^{ab}$ |
| IGF-1 | 4 | 202 | $74.8 \pm 3.6^b$ | $44.7 \pm 6.7^{ab}$ | $33.6 \pm 5.5^b$ | $34.7 \pm 7.8^b$ |
| FGF2 + LIF + IGF-1 | 4 | 199 | $88.9 \pm 3.2^a$ | $49.7 \pm 2.3^a$ | $44.2 \pm 2.6^a$ | $39.2 \pm 8.9^a$ |

*Data are reported as means ± SEM
**Oocytes were matured in chemically defined TCM-199 maturation medium (Control), or maturation medium with additional FGF2 + LIF, IGF-1, or FGF2 + LIF + IGF-1. After maturation, MII oocytes were used for IVF. IVF embryos from each group were cultured in standard MU1-PZM for six days when blastocyst formation was assessed.
$^{ab}$Different superscripts within a column denote a significant difference, P < 0.05.

TABLE 3

The in vivo developmental competence of the blastocysts produced from the oocytes treated by FGF2, LIF and IGF-1 in combination during maturation.

| Treatment | Number of Embryo Transfers | Percentage of Pregnancy | Combined Mean Litter Size |
|---|---|---|---|
| Control | 16 | (10/16) 62.5% | $4.8 \pm 0.7$ |
| FGF2 + LIF + IGF-1 | 13 | (8/13) 61.5% | $9.7 \pm 0.6$ |

Example 3

Evaluation of Cytokines in Embryo Culture Medium

When the same cytokine cocktail (40 ng/ml FGF2, 20 ng/ml LIF, and 20 ng/ml IGF-1) was added to a standard in the embryo culture medium at Day 4 after IVF, more embryos were able to develop to blastocyst stage (Table 4, column 6), indicating that the cocktail can also benefit embryo development when they were added to the embryo culture medium.

TABLE 4

Effects of FGF2, LIF and IGF on blastocyst formation when added to the culture medium on day 4 after IVF.*

| Treatment** | Replicate | Zygotes (n) | Cleavage/ Zygote (%) | Blastocysts/ Cleavage (%) | Blastocyst/ Zygote (%) |
|---|---|---|---|---|---|
| Control | 4 | 172 | $58.1 \pm 8.0$ | $54.3\ 7.8^a$ | $30.2 \pm 4.0^a$ |
| FGF2 + LIF + IGF-1 | 4 | 171 | $60.7 \pm 3.1$ | $67.5 \pm 4.4^b$ | $41.0 \pm 3.9^b$ |

*Data are reported as means ± SEM.
**Oocytes were matured in chemically defined TCM-199 maturation medium. After maturation, MII oocytes were used for IVF. Presumptive IVF zygotes were cultured in standard MU1-PZM till day 4, when the FGF2, LIF, and IGF-1 cocktail was added in the culture medium and cultured till day 6. In control group, embryos were cultured in MU1-PZM for six days when blastocyst formation was assessed.
Different superscripts within a column denote a significant difference, P < 0.05.

Example 4

Evaluation of Cytokine Combination in Other Species

Figure 3:
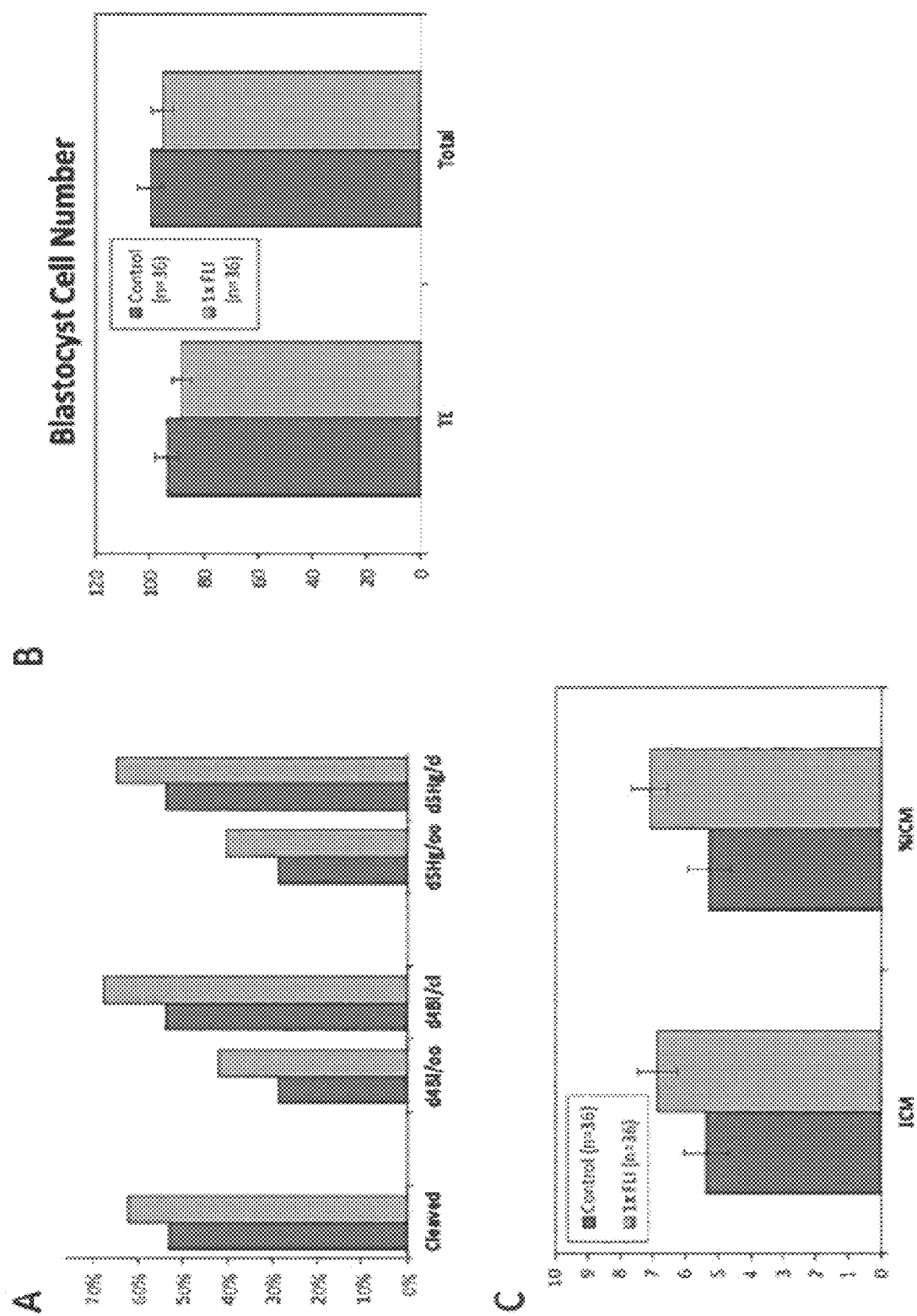
FIG. 3. Embryonic development of mouse in vitro fertilization (IVF) oocytes treated by the cocktail of three cytokines during in vitro maturation (IVM). Three replicates were performed with a total of 167-174 oocytes per treatment. The left hand bar for each set represents control oocytes; the right hand bar for each set represents oocytes treated by cytokines. The percentages of cleavage (Cleaved), percentages of blastocysts on day 4 against the total oocytes (d4Bl/oo) and against cleaved embryos (d4Bl/cl), and the percentages of hatching blastocysts on day 5 (d5Hg/oo, and d5Hg/cl) are presented in panel A. Hatching blastocysts were stained for Cdx2 and Sox2 to count the number of total cells (Total), trophectoderm cells (TE) in panel B, and the ICM cells in panel C.

The mixture of the three cytokines was assessed for its ability to aid oocyte maturation in other species. Mouse oocytes retrieved from the ovaries of CF1 outbred young female mice were matured in a defined maturation medium (1.5 mM glucose, 0.5 mM pyruvate, 4.0 mM lactate, 0.5 mM ala-gln, 1×MEM-NEAA, 0.25×MEM-EAA, 0.1 mM citrate, 10 ng/ml rmEGF, 1.5 mg/ml fetuin, and 2.5 mg/ml rHSA) in the presence or absence of FGF2 (40 ng/ml), LIF (20 ng/ml), and IGF-1 (20 ng/ml). As was observed with porcine oocytes, the matured mouse oocytes after in vitro fertilization gave rise to a significantly increased number of blastocysts on day 4 (42% versus 29% in controls,) and hatching blastocysts on day 5 (40% versus 28% in controls) (FIG. 3). Additionally, the number of the inner cell mass (ICM) cells and their percentage contribution to the whole embryo were significantly higher in the blastocysts that had been derived from oocytes matured in the new maturation medium (FIG. 3), suggesting an improved embryo quality. Preliminary embryo transfer results additionally suggest that embryos exposed to the three cytokine combination during IVM exhibit improved implantation post transfer (9 out of 14, or 64%), as compared to control (2 out of 14, or 14%).

Figure 4:
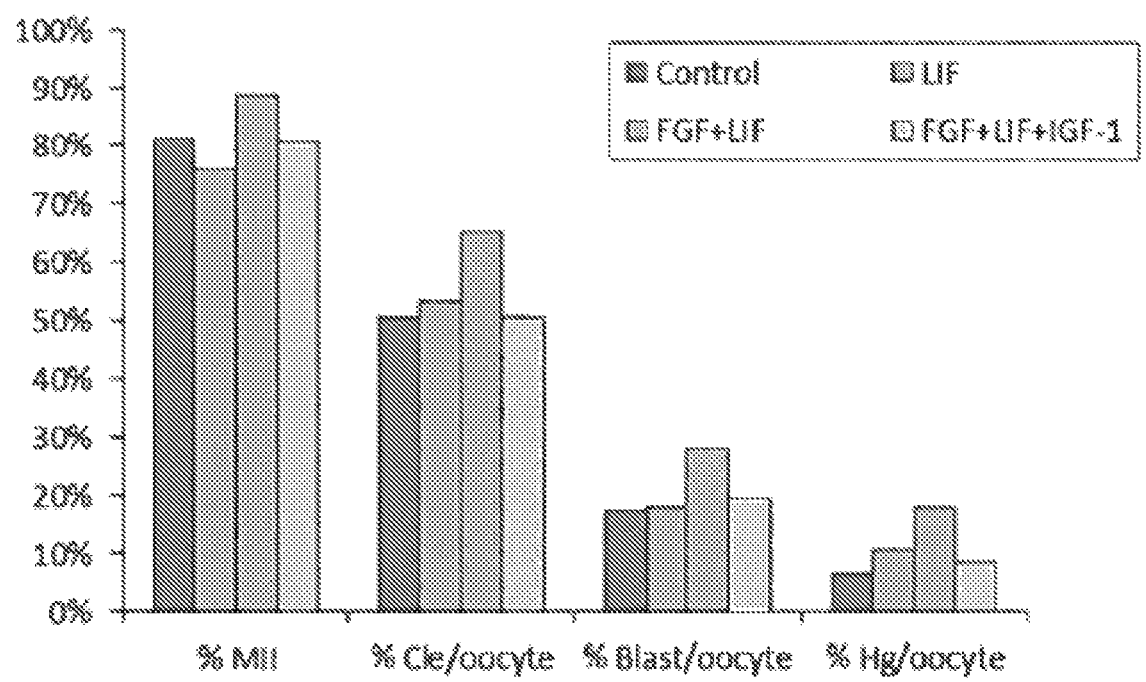
FIG. 4. The effects of different cytokine combinations during bovine oocyte IVM on nuclear maturation and subsequent developmental competence. Three replicates were performed with a total of 150 oocytes per treatment. The percentages of nuclear maturation (% MII), cleavage (% Cle/oocyte), blastocyst formation (% Blast/oocyte) and hatching blastocyst (% Hg/oocyte) were all calculated against the total oocytes used in each treatment.

The inventive maturation medium was also tested on immature bovine oocytes recovered from cow after slaughter. Bovine oocytes were collected from abattoir ovaries and shipped to the laboratory in maturation medium (5.0 mM glucose, 0.4 mM pyruvate, 6.0 mM lactate, 1.0 mM ala-gln, 1×MEM-NEAA, 0.5×MEM-EAA, 0.5 mM citrate, 50 ng/ml rmEGF, 0.1 IU/ml rhFSH, and 2.5 mg/ml rHSA) containing no growth factors, LIF, LIF+FGF2, or LIF+FGF2+IGF-1 present at the same concentrations used for murine IVM. No improvement was noted in either bovine oocyte maturation or their subsequent progression to blastocyst after in vitro fertilization of the oocytes when all three cytokines were present. However, when IGF-1 was not included, and the combination of FGF2 (40 ng/ml) and LIF (20 ng/ml) was employed, there was a slight improvement in oocyte nuclear maturation (88% versus 81% in controls), but significantly improved zygote cleavage (65% versus 50% in controls), blastocyst formation (28% versus 17% in controls), and blastocyst hatching (18% versus 6% in controls) after IVF (FIG. 4). These results suggested that the use of the prescribed oocyte maturation medium may be applicable to species other than the pig, but that concentrations may have to be optimized to obtain the best outcomes possible.

Example 5

Evaluation of SCNT with Oocytes Matured in Cytokine Supplemented IVM Medium

The ability of the improved maturation of oocytes to contribute to the efficiency of blastocyst production following SCNT with porcine fetal fibroblast donor cells was assayed. Cumulus oocyte complexes (COCs) from pre-pubertal gilts were matured in either control maturation medium or the same medium containing 40 ng/ml FGF2, 20 ng/ml LIF, and 20 ng/ml IGF-1 for 40 hr. After removing cumulus cells, MII oocytes were selected for SCNT. Presumptive zygotes were cultured in MU2 (PZM3+1.69 mM arginine+PS48) in 5% $CO_2$, 5% $O_2$, 90% $N_2$ at 38.5° C. until day 6, when blastocyst formation was assessed in four replicate experiments.

In a separate experiment embryo culture medium was also supplemented with the same three cytokines used for oocyte maturation on day 2. When oocytes were matured with the cytokine containing media there was an increase in the number of SCNT embryos that developed into the blastocyst stage (37.7%±6.9 vs. 25.8±6.9; P=0.001, n=200, 198, respectively). The overall efficiency of blastocyst production based on the starting number of COC was doubled when COCs were matured with the cytokine containing medium (21.6%±3.3 vs. 11.0%±3.3; P=0.002). Transfer of SCNT embryos that originated from maturation with the cytokine containing medium to two surrogates resulted in successful pregnancies, with an average of 6 live piglets born. In the second experiment more blastocysts developed than in unsupplemented medium (29.8%±1.1 vs.18.1%±1.1; P=0.04; 3 replicates, n-113, 114, respectively). Thus the cytokine containing medium appears to provide better cytoplasmic as well as nuclear maturation of oocytes than unsupplemented medium and the further addition of these factors on embryo culture medium lead to improved development to blastocyst.

Example 6

Evaluation of IVM Gilt Oocytes Compared to IVM Sow Oocytes

It has long been believed that oocytes obtained from sows yielded a higher level of developmental competence compared with oocytes obtained from prepubertal gilts. The ability of glit-derived and sow-derived oocytes to develop to blastocyst stage using altered maturation media was therefore assessed. For these experiments, sow-derived oocytes were obtained from Desoto Biosciences and gilt ovaries were collected from Smithfield Inc. in Milan Mo. Both sets of oocytes were in vitro matured in M199 medium supplemented with 0.57 mM cysteine, 5 µg/ml LH and FSH, and 10 ng/ml epidermal growth factor. Gilt derived media was also altered to contain 40 ng/ml FGF2, 20 ng/ml LIF, and 20 ng/ml IGF-1. Additionally, the maturation media for the sow-derived oocytes contained the addition of 5 µg/ml insulin and 10% follicular fluid.

In the first experiment, IVF was performed on oocytes from both sources per standard procedure, co-incubating the oocytes with 0.25×106 porcine semen for 4 hr, followed by washing and moving the oocytes to MU2 culture media at 38.5° C. in 5% $CO_2$, humidified air overnight. After overnight culture, the presumptive zygotes were transferred to the same conditions with 5% $CO_2$, 5% $O_2$ and 90% $N_2$. After additional 5 days, blastocyst development was assessed. The gilt oocytes yielded $39.3^a$±7.2% blastocyst, and the sow oocytes had a blastocyst rate of $24.9^b$±6.9%, with an n of 389 and 313, respectively.

In the second experiment, standard laboratory protocol for SCNT was used for activation of both sets of oocytes with 200 µM thimerosal for 10 min followed by 30 min incubation with 4 mM dithiothreitol. The embryos were co-incubated for 15 hr with 500 nM Scriptaid in the MU2 culture media in 5% $CO_2$, humidified air. These embryos were then moved to 5% $CO_2$, 5% $O_2$, and 90% $N_2$ and cultured to day 6. The sow oocytes produced a blastocyst percentage of 38.6%, and the gilt oocyte group had a blastocyst percentage of 43.5%, with an n of 290 and 285, respectively. There was no difference statistically between these treatments. Both gilt and sow oocyte sources yielded live piglets. It was concluded that the maturation system used for the gilt-derived oocytes resulted in equal or better developmental in vitro maturation compared to the sow-derived oocytes.

Example 7

Evaluation of Cytokine IVM Medium on MAPK

Figure 6:
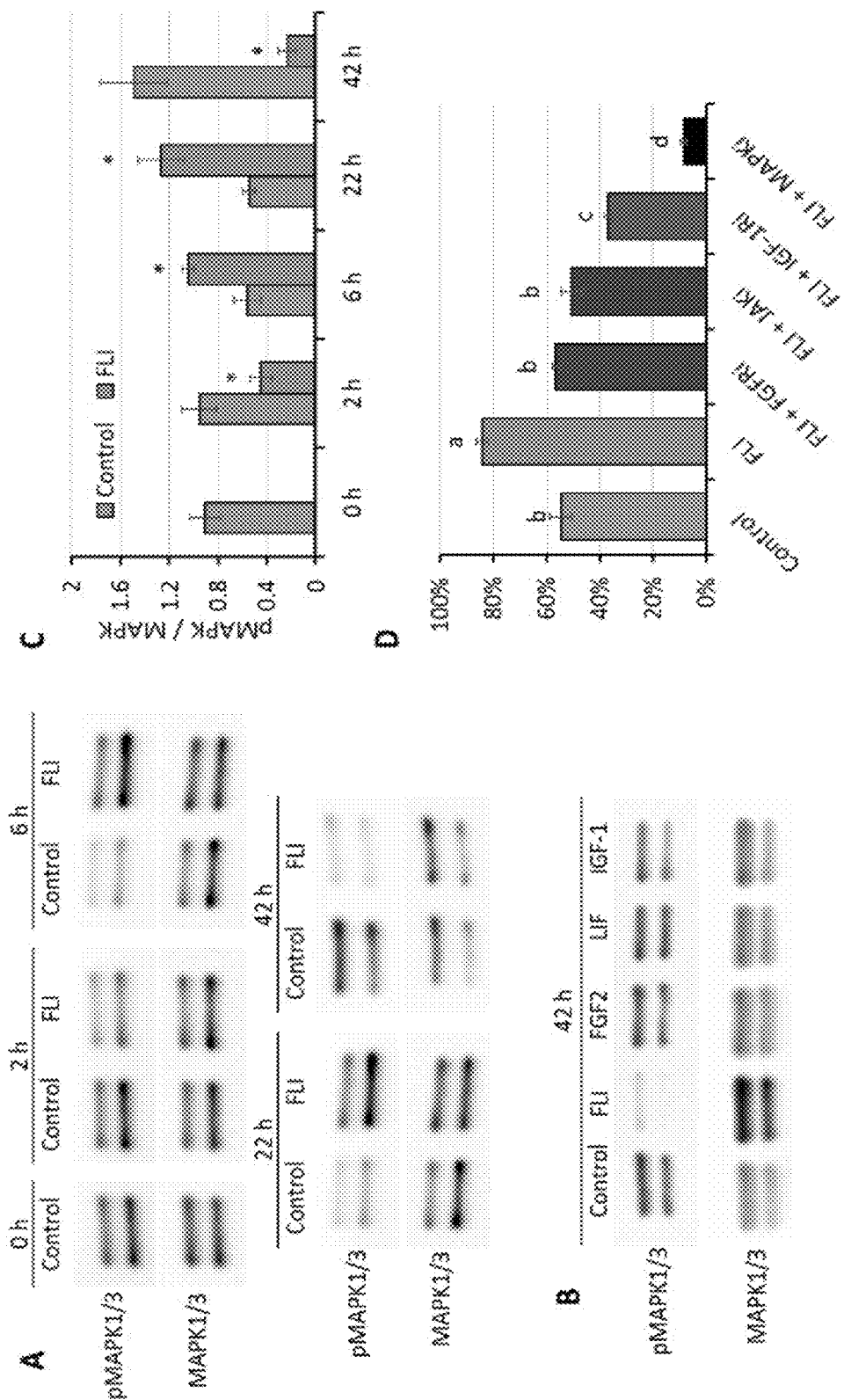
FIG. 6. Supplementation of FGF2, LIF and IGF-1 (FLI) regulates the changes of MAPK1/3 activation in cumulus cells (CCs) during IVM. Panel A shows representative images of western blots showing the effects of FGF2, LIF and IGF-1 on MAPK1/3 activity in CCs during IVM. Panel B shows effects of FGF2, LIF and IGF-1 and each individual cytokine on MAPK1/3 activity in CCs at 42 hr after IVM determined by western blot. Panel C shows the relative expression of pMAPK/MAPK was quantified and the ratios of the two forms compared between control (left bar for each set) and FGF2, LIF and IGF-1 (right bar of each set) CCs at the same time points. Each CC sample was pooled from 50 cumulus oocyte complexes (COCs). This experiment was replicated four times. Asterisk denotes a significant difference between control and treatment, P<0.05. Panel D shows the effects of adding kinase inhibitors in FGF2, LIF and IGF-1 supplemented medium on oocyte meiotic maturation. The experiments were replicated four times with 1208 oocytes. Different letters denote significant differences, P<0.05.

The fraction of phosphorylated MAPK1/3 (pMAPK1/3) relative to total MAPK1/3 (pMAPK/MAPK) during IVM in cumulus cells (CCs) was examined. At 2 hr after initiating IVM, pMAPK/MAPK was significantly reduced in the combined FGF2, LIF, and IGF-1-treated group compared with the control. Subsequently, pMAPK/MAPK levels became elevated in the combined FGF2, LIF, and IGF-1-treated group, reaching a maximum at around 22 hr. By contrast, the ratio of pMAPK to MAPK remained almost unchanged in the control over this period. However, by the end of the maturation period (42 hr), the level of pMAPK in the combined FGF2, LIF, and IGF-1-treated group had become very low, while it had continued to increase in the controls (FIG. 6). This MAPK activation pattern, involving increasing concentrations of pMAPK during the first half of oocyte maturation and almost complete loss by the end of IVM, is reminiscent of that observed in the in vivo situation in mice, and distinct from that seen in COC matured in control medium. It is important to note that this depletion of pMAPK at 42 hr is only observed in the FGF2, LIF, and IGF-1 containing medium and not when the factors are supplemented individually (FIG. 6).

In further experiments, oocytes were matured with different kinase inhibitors to block FGF2 (FGFR inhibitor, PD173074, 10 µM), LIF (JAK inhibitor I, 6 µM), and IGF-1 (IGF-1R inhibitor, OSI-906, 10 µM) signaling pathways individually and compared with data obtained when MAPK1/3 activity was directly inhibited (PD0325901, 10 µM). The MAPK inhibitor resulted in an almost complete block of meiotic maturation, whereas more moderate declines were observed when the signaling pathways initiated by the individual growth factors were inhibited (FIG. 6).

Figure 7:
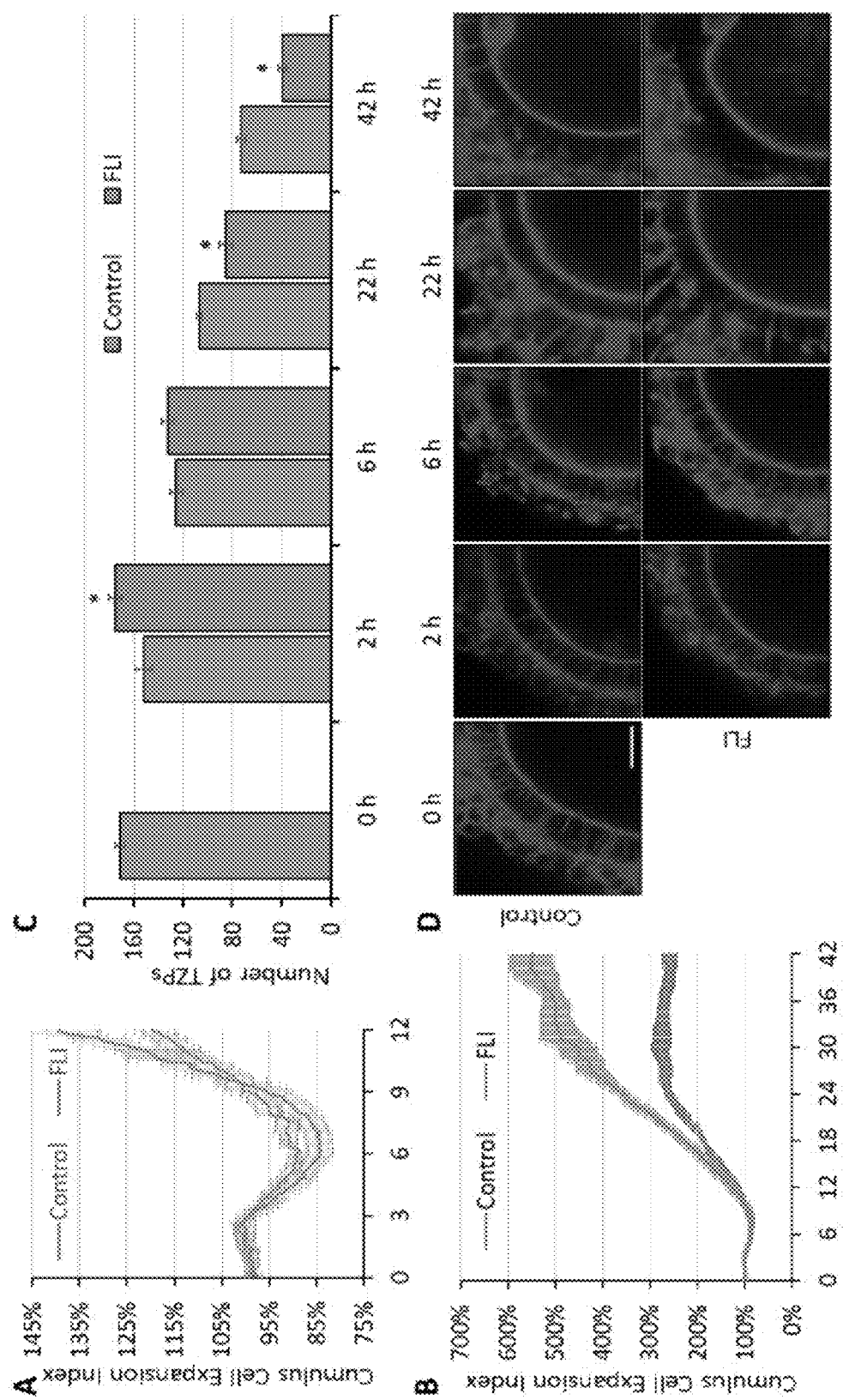
FIG. 7. Effects of FGF2, LIF and IGF-1 (FLI) on CC expansion and trans-zonal projection (TZP) integrity during IVM. Panel A shows CC expansion for the first 12 hr of IVM. The top line at 12 hr represents FGF2, LIF and IGF-1 containing medium, the bottom represents the control. Panel B shows CC expansion for the entire 42 hr IVM. The top line at 42 hr represents FGF2, LIF and IGF-1 containing medium, the bottom represents the control. Images were taken every 7.5 min and recorded by the CytoSMART system. Size of COCs was estimated by the dividing the area coverage provided by the system with the number of COCs in the images. CC Expansion Index represents the relative size of COCs relative the size of COCs at 0 hr. The experiments were replicated six times for panel A, and three times for panel B. Panel C shows the effects of FGF2, LIF and IGF-1 on TZP integrity during IVM. The left hand bar for each set represents controls; the right hand bar for each set represents treatment with cytokines. Maximum intensity projection of nine equatorial cross sections with same depth (3 μm in total) of the COCs (as shown in panel D, scale bar=20 μm) were used to measure the number of TZPs. Number of intact TZPs was compared within each time point. These experiments were replicated three times, with a total of 142 COCs. Asterisk denotes a significant difference between control and treatment, P<0.05.

Two cellular events that are mediated by MAPK activity and closely linked to the phenomenon of oocyte maturation, namely CC expansion and integrity of trans-zonal projections (TZPs), were then examined. The expansion of CCs is generally considered to be an indispensable feature accompanying oocyte meiotic maturation and tightly regulated by MAPK1/3 activity. A live imaging system (CytoSMART™ System, Lonza) was adapted to track COC expansion during IVM (FIG. 7). Surprisingly, COCs in both groups shrank in size between 3 hr and 6 hr of culture (p<0.05), a phenomenon not previously reported (FIG. 7). This decline during the initial stage of maturation, though quite small, was significantly greater in COCs cultured in medium containing FGF2, LIF, and IGF-1 (FIG. 7). After 6 hr, this process of shrinkage stopped, and the COCs from both groups began an expansion phase. This process occurred more rapidly for COCs in medium containing FGF2, LIF, and IGF-1, such that by 22 hr they had tripled in "field of view occupied"

compared to the doubling observed in controls. After 22 hr, the COCs in medium containing FGF2, LIF, and IGF-1 continued their expansion and attained an over five-fold increase in apparent diameter by the end of IVM at 42 hr IVM. By contrast, COCs in control medium reached their maximum size by about 22 hr and showed no growth thereafter. (FIG. 7).

Following the results demonstrating the changes in MAPK activity shown in FIG. 6, a comparison of the relative numbers of intact TZPs in COCs matured in medium containing FGF2, LIF, and IGF-1 versus control medium was performed. The COCs cultured in medium containing FGF2, LIF, and IGF-1 possessed significantly more TZPs at 2 hr than the controls (FIG. 7). While numbers of TZPs in both groups subsequently declined, there were significantly more TZPs remaining intact in the control group at 22 hr and 42 hr than in the COCs cultured in medium containing FGF2, LIF, and IGF-1 (FIG. 7). One consistent feature of the oocytes matured in the presence FGF2, LIF, and IGF-1 was a larger perivitelline space than observed in those matured in control medium, a phenomenon seen in oocytes matured in vivo.

Example 8

Evaluation of Cytokine IVM Medium on mRNA Levels

Figure 8:
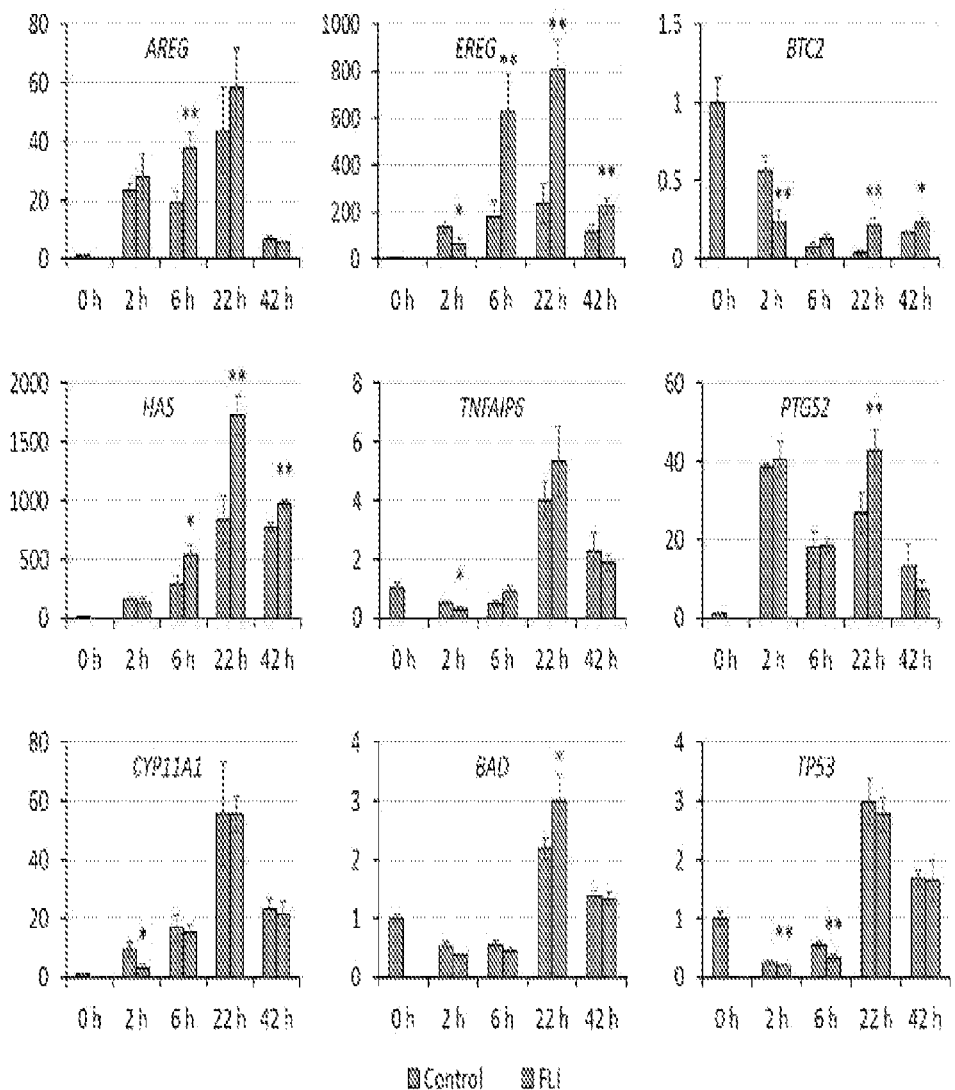
FIG. 8. Effects of FGF2, LIF and IGF-1 (FLI) on mRNA abundance of EGF like factors (AREG, EREG, BTC2), CC expansion factors (HAS, TNFAIP6, PTGS2), and stress related genes (CYP11A1, BAD, TP53) during IVM. The relative abundance of mRNA was examined by quantitative PCR and compared between control and FGF2, LIF and IGF-1 CCs within the same time point. The left hand bar for each set represents controls; the right hand bar for each set represents treatment with cytokines. The mRNA level for all the genes was arbitrary set to 1 in control at 0 hr. Data were analyzed by software REST 2009 by using CALR as the internal control. ** denotes significant differences in mRNA abundance between control and treatment, P<0.05. * denotes there was a trend to be different P<0.1. The experiments were replicated four times for time 0 hr, 2 hr, and 6 hr time points, and three times for 22 hr and 42 hr time points.

The abundance of mRNA of certain genes implicated in IVM of oocytes also correlated with the changes in the pMAPK/MAPK ratio in CCs was analyzed. Genes for EGF-like factors (AREG, EREG and BTC2), so-called CC expansion factors (HAS, TNFAIP6, and PTGS2), and stress-related genes (CYP11A1, BAD, and TP53) were analyzed throughout culture. At 2 hr, transcripts of BTC2, CYP11A1, TP53 were down-regulated ($P<0.05$), while EREG, TNFAIP6 displayed a tendency to be down-regulated ($P<0.1$) in CCs cultured in medium containing FGF2, LIF, and IGF-1, relative to controls. These data may reflect the greater shrinkage of the FGF2, LIF, and IGF-1-treated group in the initial phases of culture and that medium containing FGF2, LIF, and IGF-1 better protected the CCs from stress. The greater abundance of mRNA for AREG, EREG, and HAS at 6 hr, and of EREG, BTC2, HAS, and PTGS2 at 22 hr ($P<0.05$) is consistent with the more rapid expansion of CC in medium containing FGF2, LIF, and IGF-1, than in control medium (FIG. 8).

Example 9

Optimization of Cytokines in IVM Medium in Different Species

The optimal concentrations of FGF2 (40 ng/ml), LIF (20 ng/ml), and IGF-1 (20 ng/ml) in Examples 1 and 2 above were determined based on these cytokine's abilities to promote nuclear maturation individually, and not blastocyst quality, which was only marginally affected in the presence of the individual cytokines. It is therefore possible that the concentrations of each cytokine could be optimized when in combination.

The concentrations of FGF2, LIF, and IGF-1 in oocyte maturation medium will be optimized to obtain the most effective combination to aid oocyte maturation, enhance blastocyst development, blastocyst hatching, improved implantation, fetal development after embryo transfer, and improve overall efficiency in SCNT in other species. Varying concentrations of each of FGF2, LIF, and IGF-1, in combination, will be added to an otherwise standard oocyte maturation medium. Medium containing combinations of FGF2, LIF, and IGF-1 at differing concentrations will also be tested along with the presence and absence of follicular fluid.

Oocytes from the species to be tested, including bovine and human, will be collected and cultured in the maturation medium containing the varying concentrations of FGF2, LIF, and IGF-1, in combination. Nuclear maturation of the cultured oocytes will be determined. After maturation in the cytokine medium, oocytes will be in vitro fertilized and the resulting zygotes will be cultured under standard in vitro culture conditions until they reach blastocysts. The ability of the fertilized oocytes (zygotes) to form blastocysts after IVF will then be determined, including examining the number of blastocysts developed, and subsequently the number of hatching blastocysts. The number of the inner cell mass (ICM) cells and their percentage contribution to the whole embryo will also be determined.

Optimal combined concentrations of FGF2, LIF, and IGF-1 to be supplemented to standard oocyte maturation medium will be determined based on results from the above assays.

Example 10

Optimization of Cytokines in Embryo Culture Medium in Different Species

The cytokine combination containing FGF2 LIF, and IGF-1 will be added to a standard in the embryo culture medium in varying concentrations to obtain the most effective combination to aid in embryo development to the blastocyst stage in other species. After IVM, fertilized oocytes (zygotes) from species to be assayed, including bovine and human, will be cultured until they reach blastocysts under standard conditions in the embryo culture medium containing FGF2 LIF, and IGF-1 in varying concentrations. The ability of the fertilized oocytes (zygotes) to form blastocysts after IVF will be determined, including examining the number of blastocysts developed, and subsequently the number of hatching blastocysts. The number of the inner cell mass (ICM) cells and their percentage contribution to the whole embryo will also be determined.

Optimal combined concentrations of FGF2, LIF, and IGF-1 to be supplemented to standard embryo culture medium will be determined based on results from the above assays.

The description herein is merely exemplary in nature and, thus, variations that do not depart froth the gist of that which is de-scribed are intended to be within the scope of the teachings. Such variations are not to be regarded as a departure from the spirit and scope of the teachings.

What is claimed is:

1. A medium for culturing an oocyte comprising fibroblast growth factor 2 (FGF2), leukemia inhibitory factor (LIF), and insulin-like growth factor 1 (IGF-1), in an amount effective to provide increased maturation of an oocyte therein compared to a control medium.

2. The medium of claim 1, wherein the medium does not comprise follicular fluid.

3. The medium of claim 1, wherein the medium provides increased advancement of an oocyte cultured therein to the blastocyst stage compared to a control medium.

4. The medium of claim 1, wherein the medium supports in vitro fertilization of an oocyte performed therein.

5. The medium of claim 1, wherein the medium supports culture of a cumulus oocyte complex cultured therein.

6. The medium of claim 1, wherein the medium is a liquid medium.

7. The medium of claim 1, wherein the medium comprises a solid support.

8. The medium of claim 1, wherein the medium comprises an oocyte.

9. The medium of claim 1, wherein the medium comprises a plurality of oocytes.

10. A method of oocyte maturation, said method comprising contacting an immature oocyte with the medium of claim 1.

11. A method of improving the developmental competence of an oocyte or an embryo produced from an oocyte, said method comprising contacting an oocyte with the medium of claim 1.

12. A method of embryo transfer, said method comprising:
a) contacting an oocyte with the medium of claim 1;
b) producing an embryo from said oocyte; and
c) transferring said embryo to the uterus of a recipient female.

13. A method of assisted reproduction, said method comprising contacting an oocyte with the medium of claim 1.

14. The method of claim 13, wherein the assisted reproduction comprises in vitro fertilization.

15. The method of claim 13, wherein the assisted reproduction comprises somatic cell nuclear transfer (SCNT).

16. A medium for culturing an embryo comprising fibroblast growth factor 2 (FGF2), leukemia inhibitory factor (LIF), and insulin-like growth factor 1 (IGF-1), in an amount effective to provide increased zygote development to a blastocyst compared to a control medium.

17. The medium of claim 16, wherein the medium is a liquid medium.

18. The medium of claim 16, wherein the medium comprises a solid support.

19. The medium of claim 16, wherein the medium comprises a zygote or an embryo.

20. The medium of claim 16, wherein the medium comprises a plurality of zygotes or embryos.

21. A method of improving developmental competence of an embryo, said method comprising contacting a zygote or an embryo with the medium of claim 16.

22. A method of embryo transfer, said method comprising contacting an embryo with the medium of claim 16 prior to transfer of said embryo to the uterus of a recipient female.

* * * * *